United States Patent [19]
Abramovitz et al.

[11] Patent Number: 5,869,281
[45] Date of Patent: Feb. 9, 1999

[54] DNA ENCODING PROSTAGLANDIN RECEPTOR FP

[75] Inventors: Mark Abramovitz; Richard Grygorczyk, both of Dollar des Ormeaux; Kathleen Metters, Montreal; Truyen Nguyen, Dorval; Thomas H. Rushmore, Dollar des Ormeaux; Deborah Slipetz, Outremont, all of Canada

[73] Assignee: Merck Frosst Canada Inc., Kirkland, Canada

[21] Appl. No.: 83,741

[22] Filed: Jun. 25, 1993

[51] Int. Cl.$^6$ .......................... C12N 15/12; C07K 14/705
[52] U.S. Cl. ................ 435/69.1; 435/252.3; 435/254.11; 435/325; 536/23.5
[58] Field of Search ............................... 435/69.1, 240.1, 435/320.1, 252.3, 70.1, 240.2, 254.11, 325; 536/23.1, 23.5

[56] References Cited

PUBLICATIONS

Balapure et al., Biology of Reproduction, 41, 385–392, 1989.
Masu et al., Nature, v. 329, p. 836, 1987.
R. Coleman, et al., Characterisation Of The Prostanoid Receptors Mediating Contraction of Guinea–Pig Isolated Trachea, (1985), Prostaglandins, 29, pp. 363–375.
P. Davies, et al., Prostaglandins and Inflammation, (1992), Inflammation: Basic Principles And Clinical Correlates, Gallin, Goldstein, Snyderman, eds., 2nd Ed., pp. 123–138.
E. Horton, et al., Uterine Luteolytic Hormone: A Physiological Role for Prostaglandin F2a, (1976), Physiol. Rev., 56, pp. 595–651.
D. DeWitt, Prostaglandin endoperoxide synthase: regulation of enzyme expression, (1991), Biochim. Biophys, Acta, 1083, pp. 121–134.
J. Stjernschantz, et al., Phenyl substituted prostaglandin analogs for glaucoma treatment, (1992), Drugs Future, 17, pp. 691–704.
P. Racz, et al., Maintained Intraocular Pressure Reduction With Once–a–Day Application of a New Prostaglandin F2a Analogue (PhXA41), (1993), Arch. Opthalmol., 111, pp. 657–661.
J. Senior, et al., In vitro characterization of prostanoid FP–, DP–, IP– and TP–receptors on the non–pregnant human myometrium, (1992), Brit. J. Pharmacol., 107, pp. 215–221.
J. Senior, et al., In vitro characterization of prostanoid receptors on human myometrium at term pregnancy, (1993), Brit. J. Pharmacol., 108, pp. 501–506.
J. Csepli, et al., The Effect Of The Prostaglandin F2a Analogue ICI 81008 On Uterine Small Arteries And On Blood Pressure, (1975), Prostaglandins, 10, pp. 689–697.
R. Coleman, Methods in prostanoid receptor classification, (1987), Prostaglandins And Related Substances—A Practical Approach, IRL Press, 1st Ed., pp. 267–303.
R. Coleman, et al., A study of the prostanoid receptors mediating bronchocorstriction in the anaesthetized guinea–pig and dog, (1981), Brit. J. Pharmacol., 74, p. 913.

J. Barnard, et al., Evaluation of prostaglandin F2a and prostacyclin interactions in the isolated perfused rat lung, (1992), J. Appl. Physiol., 72, pp. 2469–2474.
J. Davis, et al., Prostaglandin F2a stimulates phosphatidylinositol 4,5–bisphosphate hydrolysis and mobilizes intracellular Ca2+ in bovine luteal cells, (1987), Proc. Natl. Acad. Sci. U.S.A., 84, pp. 3728–3732.
J. Kitanaka, et al., Astrocytes Possess Prostaglandin F2a Receptors Coupled To Phospholipase C, (1991), Biochem. Biophys. Res. Comm., 178, pp. 946–952.
F. Black, et al., Activation of inositol phospholipid breakdown by prostaglandin F2a without any stimulation of proliferation in quiescent NIH–3T3 fibroblasts, (1990), Biochem. Journal, 266, pp. 661–667.
A. Nakao, et al., Characterization of Prostaglandin F2a Receptor of Mouse 3T3 Fibroblasts and Its Functional Expression in *Xenopus Laevis* Oocytes, (1993), J. Cell Physiol., 155, pp. 257–264.
W. Powell, et al., Prostaglandin F2a Receptor in Ovine corpora lutea, (1974), Eur. J. Biochem., 41, pp. 103–107.
W. Powell, et al., Occurrence and Properties of a Prostaglandin F2a Receptor in Bovine Corpora Lutea, (1975), Eur. J. Biochem., 56, pp. 73–77.
W. Powell, et al., Localization of a Prostaglandin F2a Receptor in Bovine *Corpus luteum* Plasma Membranes, (1976), Eur. J. Biochem., 61, pp. 605–611.
M. Molnar, et al., PGF2a and PGE2 binding to rat myometrium during gestation, parturition, and postpartum, (1990), Am. J. Physiol., 258, pp. E740–E747.
Th. Bauknecht, et al., Distribution of prostaglandin E2 and prostaglandin F2a receptors in human myometrium, (1981), Acta Endocrinol., 98, pp. 446–450.
F. Neuschafer–Rube, et al., Characterization of prostaglandin–F2a–binding sites on rat hepatocyte plasma membranes, (1993), Eur. J. Biochem., 211, pp. 163–169.
M. Hirata, et al., Cloning and expression of cDNA for a human thromboxane A2 receptor, (1991), Nature, 349, pp. 617–620.
A. Honda, et al., Cloning and Expression of a cDNA for Mouse Prostaglandin E Receptor EP2 Subtype*, (1993), J. Biol. Chem., 268, pp. 7759–7762.
Y. Sugimoto, et al., Two Isoforms of the EP3 Receptor with Different Carboxyl–terminal Domains, (1993), J. Biol. Chem., 268, pp. 2712–2718.
Y. Sugimoto, et al., Cloning and Expression of a cDNA for Mouse Prostaglandin E Receptor EP3 Subtype*, (1992), J. Biol. Chem., 267, pp. 6463–6466.
K. Bunce, et al., Differential Effects Of Prostaglandins On Unidirectional Absorption And Secretion In Rat Ileum, (1987), Gastroenterology, 92, p. 1332.

(List continued on next page.)

*Primary Examiner*—Sally P. Teng
*Attorney, Agent, or Firm*—J. Mark Hand; Jack L. Tribble

[57] ABSTRACT

A novel prostaglandin receptor has been identified and DNA encoding the receptor has been isolated, purified, sequenced and expressed in host cells. This DNA encoding the novel prostaglandin receptor and host cells expressing the receptor are used to identify modulators of the prostaglandin receptor.

5 Claims, 6 Drawing Sheets

OTHER PUBLICATIONS

Y. Dong, et al., Prostaglandin E receptor subtypes in smooth muscle: agonist activities of stable prostacyclin analogues, (1986), Br. J. Pharmacol., 87, pp. 97–107.

B. Hedqvist, et al., Prostaglandin–Induced Neurotransmission Failure In The Field–Stimulated, Isolated Vas Deferens, (1972), neuropharmacology, 11, pp. 177–187.

M. McKenniff, et. al., Characterisation of receptors mediating the contractile effects of prostanoids in guinea–pig and human airways, (1988), Eur. J. Pharmacol., 153, pp. 149–159.

R. Eglen, et al., The action of prostanoid receptor agonists and antagonists on smooth muscle and platelets, (1988), Br. J. Pharmacol., 94, pp. 591–601.

J. Louttit, et al., Prostanoid EP–Receptors In Pig Saphenous Vein, (Jul. 26–31, 1992), 8th International Conf. on Prostaglandins, Abstract 258.

R. Lawrence, et al., Investigation of the prostaglandin E (EP–) receptor subtype mediating relaxation of the rabbit jugular vein, (1992), Br. J. Pharmacol., 105, pp. 817–824.

R. Coleman, et al., Prostanoids and their Receptors, (1989), Comprehensive Medicinal Chemistry, 3, pp. 643–714.

W. Campbell, et al., Lipid–Derived Autacoids: Eicosanoids And Platelet–Activating Factor, (1990), The Pharmacological Basis of Therapeutics, 8th Edition, pp. 600–617.

Kitanaka, Junichi et al., Desensitization of glial prostaglandin F2a receptors, Jpn. J. Pharmacol., Suppl. 1, 61; p. 85P, (1993). Abstract 0–75.

```
GTGCGCGGAGGGGACGAGCGGCTGGACCACAGCCGGCGCCCGATCAGGATCTCCGCG
CTGGGATCGGTGGAACTTGAGGCAGCGGCGGCGCGGGGCGCCATGGCACACCGAGCG
GCTCCGTCTTCTGCTCCTCAGAGAGCCCGGCTGGCGGCCTGGGATGACAAGATGTCT
GGACTGCAATCCTGCACAGTTTTGAGAGGGAGATGACTTGAGTGGTTGGCTTTTATC
TCCACAACAATGTCCATGAACAATTCCAAACAGCTAGTGTCTCCTGCAGCTGCGCTT
CTTTCAAACACAACCTGCCAGACGGAAAACCGGCTTTCCGTATTTTTTTCAGTAATC
TTCATGACAGTGGGAATCTTGTCAAACAGCCTTGCCATCGCCATTCTCATGAAGGCA
TATCAGAGATTTAGACAGAAGTCCAAGGCATCGTTTCTGCTTTTGGCCAGCGGCCTG
GTAATCACTGATTTCTTTGGCCATCTCATCAATGGAGCCATAGCAGTATTTGTATAT
GCTTCTGATAAAGAATGGATCCGCTTTGACCAATCAAATGTCCTTTGCAGTATTTTT
GGTATCTGCATGGTGTTTTCTGGTCTGTGCCCACTTCTTCTAGGCAGTGTGATGGCC
ATTGAGCGGTGTATTGGAGTCACAAAACCAATATTTCATTCTACGAAAATTACATCC
AAACATGTGAAAATGATGTTAAGTGGTGTGTGCTTGTTTGCTGTTTTCATAGCTTTG
CTGCCCATCCTTGGACATCGAGACTATAAAATTCAGGCGTCGAGGACCTGGTGTTTC
TACAACACAGAAGACATCAAAGACTGGGAAGATAGATTTTATCTTCTACTTTTTTCT
TTTCTGGGGCTCTTAGCCCTTGGTGTTTCATTGTTGTGCAATGCAATCACAGGAATT
ACACTTTTAAGAGTTAAATTTAAAAGTCAGCAGCACAGACAAGGCAGATCTCATCAT
TTGGAAATGGTAATCCAGCTCCTGGCGATAATGTGTGTCTCCTGTATTTGTTGGAGC
CCATTTCTGGTTACAATGGCCAACATTGGAATAAATGGAAATCATTCTCTGGAAACC
TGTGAAACAACACTTTTTGCTCTCCGAATGGCAACATGGAATCAAATCTTAGATCCT
TGGGTATATATTCTTCTACGAAAGGCTGTCCTTAAGAATCTCTATAAGCTTGCCAGT
CAATGCTGTGGAGTGCATGTCATCAGCTTACATATTTGGGAGCTTAGTTCCATTAAA
AATTCCTTAAAGGTTGCTGCTATTTCTGAGTCACCAGTTGCAGAGAAATCAGCAAGC
ACCTAGCTTAATAGGACAGTAAATCTGTGTGGGGCTAGAACAAAAATTAAGACATGT
TTGGCAATATTTCAGTTAGTTAAATACCTGTAGCCTAACTGGAAAATTCAGGCTTCA
TCATGTAGTTTG (SEQ ID NO:4)
```

FIG. 1

MSMNNSKQLVSPAAALLSNTTCQTENRLSVFFSVIFMTVGILSNSLAIAI
LMKAYQRFRQKSKASFLLLASGLVITDFFGHLINGAIAVFVYASDKEWIR
FDQSNVLCSIFGICMVFSGLCPLLLGSVMAIERCIGVTKPIFHSTKITSK
HVKMMLSGVCLFAVFIALLPILGHRDYKIQASRTWCFYNTEDIKDWEDRF
YLLLFSFLGLLALGVSLLCNAITGITLLRVKFKSQQHRQGRSHHLEMVIQ
PWVYILLRKAVLKNLYKLASQCCGVHVISLHIWELSSIKNSLKVAAISES
PVAEKSAST (SEQ ID NO:5)

FIG.2

DNA ENCODING PROSTAGLANDIN RECEPTOR FP

BACKGROUND OF THE INVENTION

The physiological actions of prostaglandin (PG)$F_{2\alpha}$ are mediated through interaction with the prostaglandin $F_{2\alpha}$ (FP) receptor. This receptor has not previously been isolated or purified. FP-encoding DNA and the amino acid sequence of the FP receptor protein was also not known FP receptors are normally found on a wide variety of cells and tissues including the small intestine, corpus luteum, placenta, ovary, brain, myometrium, lung, kidney, stomach, muscle, eye, uterus and trachea, in humans and other animals. Binding of prostaglandin to the FP receptor protein elicits an increase in intracellular calcium levels. This signal causes the tissues to respond, for example, by muscle contraction and in the eye indirectly causes a reduction in intraocular pressure. Studies on $PGF_{2\alpha}$ binding sites (FP receptors) have been performed using primarily corpus lutea tissue since $PGF_{2\alpha}$ is a potent luteolytic agent [Powell et al, 1974 Lancet, 1, pp 1120; Powell et al., 1974, Eur. J. Biochem., 41, pp 103–107]. Functional activities of the FP receptor have been studied using tissue preparations such as rabbit jejunum and the cat, bullock and dog iris sphincter tissues [Dong and Jones, 1982 Br. J. Pharmac., 76, pp 149–155; Welburm and Jones, 1978Prostaglandins, 15, pp 287]. The above methods for studying FP receptor activities have several disadvantages in that they require tissue preparations containing several different but related receptor populations with different ligand binding properties making absolute potency and selectivity impossible. In addition, tissues contain very low levels of FP receptor and since tissue samples are required, compounds cannot satisfactorily be tested as effectors of the human FP receptor.

SUMMARY OF THE INVENTION

A novel prostaglandin receptor protein termed FP has been identified from human cells. A DNA molecule encoding the full length FP protein has been isolated and purified, and the nucleotide sequence has been determined. The FP encoding DNA has been cloned into expression vectors and these expression vectors, when introduced into recombinant host cells, cause the recombinant host cells to express a functional FP receptor protein. The novel FP protein, the FP-encoding DNA, the expression vectors and recombinant host cells expressing recombinant FP are useful in the identification of modulators of FP receptor activity.

A method of identifying FP receptor modulators is also disclosed which utilizes the recombinant FP expressing host cells. Modulators of FP activity are useful for the treatment of prostaglandin-related diseases and for modulating the effects of prostaglandins on the FP receptor.

BRIEF DESCRIPTION OF THE DRAWINGS

FIG. 1 - The complete DNA sequence encoding the FP receptor protein is shown (SEQ ID NO:4).

FIG. 2 - The complete deduced amino acid sequence of the FP receptor protein is shown(SEQ ID NO:5).

DETAILED DESCRIPTION OF THE INVENTION

Figure 3A:
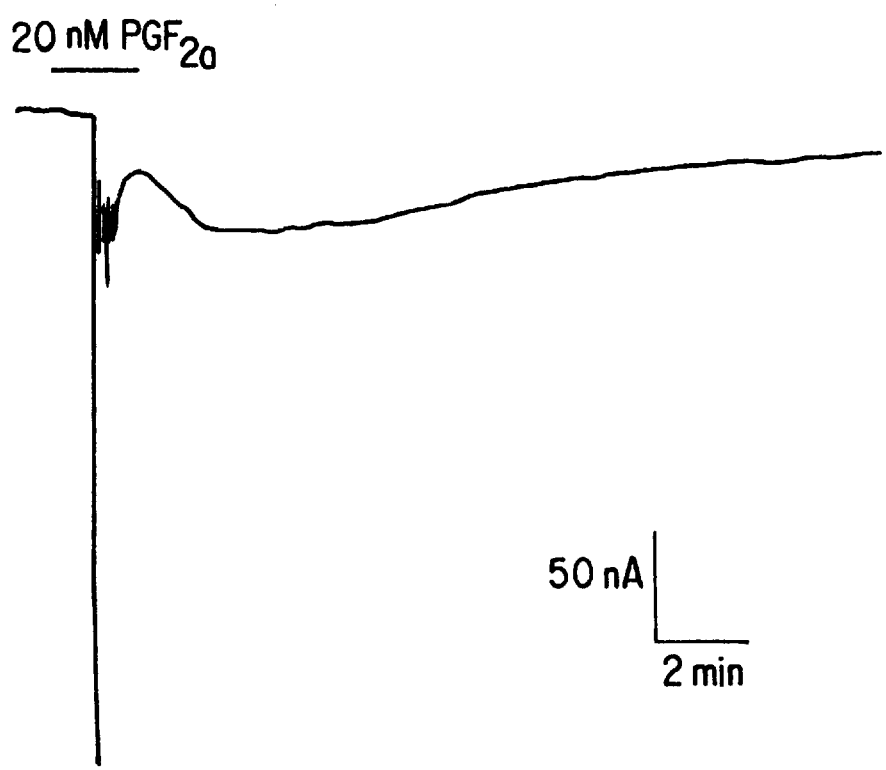
FIGS. 3A and 3B - Expression of the prostaglandin $F_{2\alpha}$ receptor in FP cDNA-injected Xenopus oocytes. An inward $Ca^{2+}$-dependent Cl-current (shown as downward deflection) evoked by bath perfusion of 20 nM $PGF_{2\alpha}$ (upper trace FIG. 3A) and 10 nM of fluprostenol (lower trace FIG. 3B). The oocyte was injected with 1 ng FP cDNA and voltage-clamped at −60 mV.

The present invention relates to cDNA encoding a novel prostaglandin receptor termed FP. The present invention is also related to recombinant host cells which express the cloned FP-encoding DNA contained in a recombinant expression plasmid. The present invention is also related to a method for the screening of substances which modulate FP receptor activity. The DNA of the present invention is isolated from FP producing cells. FP, as used herein, refers to a G protein-coupled receptor which can specifically bind prostaglandin molecules.

Mammalian cells capable of producing FP include, but are not limited to, cells derived from small intestine, kidney, stomach, muscle, eye, placenta, uterus and trachea. Transformed mammalian cell lines which produce FP include, but are not limited to, 3T3 fibroblasts cells. The preferred cells for the present invention include normal human kidney and placental cells and the most preferred cells are human corpora lutea cells.

Other cells and cell lines may also be suitable for use to isolate FP cDNA. Selection of suitable cells may be done by screening for FP on cell surfaces. Methods for detecting FP activity are well known in the art and measure the binding of radiolabelled ligand specific for the receptor. Cells which possess FP activity in this assay may be suitable for the isolation of FP cDNA.

Any of a variety of procedures may be used to clone FP cDNA. These methods include, but are not limited to, direct functional expression of the FP cDNA following the construction of an FP-containing cDNA library in an appropriate expression vector system. Another method is to screen an FP-containing cDNA library constructed in a bacteriophage or plasmid shuttle vector with a labelled oligonucleotide probe designed from the amino acid sequence of the FP protein. The preferred method consists of screening an FP-containing cDNA library constructed in a bacteriophage or plasmid shuttle vector with a partial cDNA encoding the FP protein. This partial cDNA is obtained by the specific PCR amplification of FP DNA fragments through the design of degenerate oligonucleotide primers from the amino acid sequence known for other G protein-coupled receptors which are related to the prostaglandin FP receptors.

It is readily apparent to those skilled in the art that other types of libraries, as well as libraries constructed from other cells or cell types, may be useful for isolating FP-encoding DNA. Other types of libraries include, but are not limited to, cDNA libraries derived from other cells or cell lines and genomic DNA libraries.

It is readily apparent to those skilled in the art that suitable cDNA libraries may be prepared from cells or cell lines which have FP activity. The selection of cells or cell lines for use in preparing a cDNA library to isolate FP cDNA may be done by first measuring cell associated FP activity using the known labelled ligand binding assay cited above and used herein.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual (Cold Spring Harbor Laboratory, Cold Spring Harbor, N.Y., 1982).

It is also readily apparent to those skilled in the art that DNA encoding FP may also be isolated from a suitable genomic DNA library. Construction of genomic DNA libraries can be performed by standard techniques well known in the art. Well known genomic DNA library construction techniques can be found in Maniatis, T., Fritsch, E. F., Sambrook, J. in Molecular Cloning: A Laboratory Manual (Cold Spring Harbor Laboratory, Cold Spring Harbor, N.Y., 1982).

In order to clone the FP gene by one of the preferred methods, the amino acid sequence or DNA sequence of FP or a homologous protein is necessary. To accomplish this, FP protein or a homologous protein may be purified and partial amino acid sequence determined by automated sequenators. It is not necessary to determine the entire amino acid sequence, but the linear sequence of two regions of 6 to 8 amino acids can be determined for the PCR amplification of a partial FP DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the FP sequence but others in the set will be capable of hybridizing to FP DNA even in the presence of DNA oligonucleotides with mismatches. The mismatched DNA oligonucleotides may still sufficiently hybridize to the FP DNA to permit identification and isolation of FP encoding DNA.

Using one of the preferred methods, cDNA clones encoding FP are isolated in a two-stage approach employing polymerase chain reaction (PCR) based technology and cDNA library screening. In the first stage, $NH_2$-terminal and internal amino acid sequence information from the purified FP or a homologous protein is used to design degenerate oligonucleotide primers for the amplification of FP-specific DNA fragments. In the second stage, these fragments are cloned to serve as probes for the isolation of full length cDNA from a cDNA libraries.

The sequence for the near full-length cDNA encoding FP is shown in Table 1, and was designated clone FP. The deduced amino acid sequence of FP from the cloned cDNA is shown in Table 2. Inspection of the determined cDNA sequence reveals the presence of a single, large open reading frame that encodes for a 359 amino acid protein.

The cloned FP cDNA obtained through the methods described above may be recombinantly expressed by molecular cloning into an expression vector containing a suitable promoter and other appropriate transcription regulatory elements, and transferred into prokaryotic or eukaryotic host cells to produce recombinant FP. Techniques for such manipulations can be found described in Maniatis, T, et al., supra, and are well known in the art.

Expression vectors are defined herein as DNA sequences that are required for the transcription of cloned DNA and the translation of their mRNAs in an appropriate host. Such vectors can be used to express eukaryotic DNA in-a variety of hosts such as bacteria, bluegreen algae, plant cells, insect cells and animal cells.

Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant FP in mammalian cells. Commercially available mammalian expression vectors which may be suitable for recombinant FP expression, include but are not limited to, pMC1neo (Stratagene), pXT1 (Stratagene), pSG5 (Stratagene), pcDNAI, pcDNAIamp (Invitrogen), EBO-pSV2-neo (ATCC 37593) pBPV-1(8-2) (ATCC 37110), pdBPV-MMTneo(342-12) (ATCC 37224), pRS-Vgpt (ATCC 37199), pRSVneo (ATCC 37198), pSV2-dhfr (ATCC 37146), pUCTag (ATCC 37460), and IZD35 (ATCC 37565)

DNA encoding FP may also be cloned into an expression vector for expression in a host cell. Host cells may be prokaryotic or eukaryotic, including but not limited to bacteria, yeast, mammalian cells including but not limited to cell lines of human, bovine, porcine, monkey and rodent origin, and insect cells including but not limited to drosophila derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techniques including but not limited to transformation, transfection, protoplast fusion, and electroporation. The expression vector-containing cells are individually analyzed to determine whether they produce FP protein. Identification of FP expressing cells may be done by several means; including but not limited to immunological reactivity with anti-FP antibodies, and the presence of host cell-associated FP activity.

Expression of FP DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the FP cDNA sequence(s) that yields optimal levels of receptor activity and/or FP protein, FP cDNA molecules including but not limited to the following can be constructed: the full-length open reading frame of the FP cDNA and various constructs containing portions of the cDNA encoding only specific domains of the receptor protein or rearranged domains of the protein. All constructs can be designed to contain none, all or portions of the 5' and/or 3' untranslated region of FP cDNA. FP activity and levels of protein expression can be determined following the introduction, both singly and in combination, of these constructs into appropriate host cells. Following determination of the FP cDNA cassette yielding optimal expression in transient assays, this FP cDNA construct is transferred to a variety of expression vectors (including recombinant viruses), including but not limited to those for mammalian cells, plant cells, insect cells, oocytes, *E. coli*, and yeast cells.

Mammalian cell transfectants are assayed for both the levels of FPreceptor activity and levels of FP protein by the following methods. Assessing FP receptor activity involves the direct introduction of a labelled ligand to the cells and determining the amount of specific binding of the ligand to the FP-expressing cells. Binding assays for receptor activity are known in the art (Frey et al., 1993, Eur. J. Pharmacol., 244, pp 239–250).

Levels of FP protein in host cells is quantitated by a variety of techniques including, but not limited to, immunoaffinity and/or ligand affinity techniques. FP-specific affinity beads or FP-specific antibodies are used to isolate $^{35}S$-methionine labelled or unlabelled FP protein. Labelled FP protein is analyzed by SDS-PAGE. Unlabelled FP protein is detected by Western blotting, ELISA or RIA assays employing FP specific antibodies.

Following expression of FP in a host cell, FP protein may be recovered to provide FP in active form, capable of binding FP-specific ligands. Several FP purification procedures are available and suitable for use. Recombinant FP may be purified from cell membranes by various combinations of, or individual application of standard separation techniques including but not limited to detergent solubilization, salt fractionation, ion exchange chromatography, size exclusion chromatography, hydroxylapatite adsorption chromatography and hydrophobic interaction chromatography.

In addition, recombinant FP can be separated from other cellular proteins by use of an immuno-affinity column made with monoclonal or polyclonal antibodies specific for full length nascent FP, or polypeptide fragments of FP.

Monospecific antibodies to FP are purified from mammalian antisera containing antibodies reactive against FP or are prepared as monoclonal antibodies reactive with FP using the technique of Kohler and Milstein, Nature 256: 495–497 (1975). Monospecific antibody as used herein is defined as a single antibody species or multiple antibody species with homogenous binding characteristics for FP. Homogenous binding as used herein refers to the ability of the antibody species to bind to a specific antigen or epitope, such as those associated with the FP, as described above. FP specific antibodies are raised by immunizing animals such as mice, rats, guinea pigs, rabbits, goats, horses and the like, with an appropriate concentration of FP or a peptide derived from the sequence of the FP protein either with or without an immune adjuvant.

Preimmune serum is collected prior to the first immunization. Each animal receives between about 0.1 mg and about 1000 mg of FP or FP-related peptide associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consisted of the enzyme in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunizaiton. Those animals receiving booster injections are generally given an equal amount of FP or FP-related peptide in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with FP or a peptide derived from the sequence of the FP protein are prepared by immunizing inbred mice, preferably Balb/c, with FP or FP-related peptide . The mice are immunized by the IP or SC route with about 1 mg to about 100 mg, preferably about 10 mg, of FP or FP-related peptide in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 mg of FP in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS 1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using FP or FP-related peptide as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection, of pristine primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-FP mAb is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of FP in body fluids or tissue and cell extracts.

It is readily apparent to those skilled in the art that the above described methods for producing monospecific antibodies may be utilized to produce antibodies specific for FP polypeptide fragments, or full-length FP polypeptide.

FP antibody affinity columns are made by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) together with appropriate membrane solubilizing such as detergents and the cell culture supernatants or cell extracts containing FP or FP fragments are slowly passed through the column. The column is then washed with phosphate buffered saline together with appropriate membrane solubilizing such as detergents until the optical density ($A_{280}$) falls to background, then the protein is eluted with 0.23M glycine-HCl (pH 2.6) together with appropriate membrane solubilizing such as detergents. The purified FP protein is then dialyzed against phosphate buffered saline together with appropriate membrane solubilizing such as detergents.

One method suitable for the isolation of DNA encoding the prostaglandin receptor of the present invention involves the utilization of amino acid and/or DNA sequence information obtained from other G-protein-linked receptors. Since other prostaglandin receptors are known to be G-protein linked, certain regions or domains such as the transmembrane and/or cytoplasmic domains, are expected to have some degree of homology sufficient to produce a probe for the isolation of novel receptors.

Prostaglandins and leukotrienes are known to transduce their signals via G-protein-linked receptors. Distinct receptors for $PGH_2$/thromboxane $A_2$, $PGI_2$, $PGE_2$, $PGD_2$, $PGF_{2\alpha}$, $LTB_4$, and $LTD_4$ present in various tissues have been described. Some of the receptors have been solubilized and partially purified ( Dutta-Roy, A. K. et al., (1987) JBC, 262, pp. 12685; Tsai, A. L. et al., (1989), JBC, 264, pp 61; 168—Watawabe, T. et. al., (1990), JBC, 265, pp. 21237) and the human platelet $TXA_2$ receptor has been purified to apparent homogeneity (Ushikubi, F. et. al., (1989), JBC, 264, pp. 16496). The purified thromboxane receptor exhibited a very broad band on a SDS-polyacrylamide gel centered at "57 kDa. Enough protein was obtained for partial sequence information.

An approach to the isolation of other eicosanoid receptor genes by homology screening was taken, with the assumption that these receptors are related in primary structure (Sugimoto, Y. et al., (1992), JBC, 267, pp. 6463). Since these receptors are of the G-protein-coupled receptor superfamily there are areas of homology which are likely to be found in the transmembrane region and in the cytoplasmic domains. Therefore, various known G-protein linked receptors related to the prostaglandin receptors may be utilized to provide DNA probes to regions of the receptor protein-encoding DNA sought, which is likely to have homology, such as the transmembrane region.

Using a 0.37-kb fragment of a putative mouse FP receptor cDNA which encodes most of the transmembrane 5–7 region of this receptor was used to screen a human kidney library from which a partial human FP cDNA was isolated. This in turn was used to obtain a 2.5-kb cDNA clone hereinafter designated FP encoding a 359-amino acid receptor was isolated from a human uterus cDNA library. This protein was designated as the FP receptor. Like many other G-protein coupled receptors the FP receptor shares several common features. Firstly, there are 3 potential N-linked glycosylation sites (Asn4, Asn19) and Asn277 in the putative extracellular amino- terminus. Secondly, conserved cysteine residues are found in exofacial loops 1 and 2. There are multiple serine residues, potential sites of protein kinase phosphorylation, throughout the C-terminus and third cytoplasmic loops. The FP receptor does not contain an aspartic acid residue in transmembrane three which is characteristic of the receptors binding cationic amino-containing ligands, however, it possesses a conserved arginine (position 295) found in all known eicosanoid receptors within transmembrane seven. This region is the most highly conserved among the eicosanoid receptors.

The novel prostaglandin receptor of the present invention is suitable for use in an assay procedure for the identification of compounds which modulate the receptor activity. Modulating receptor activity, as described herein includes the inhibition or activation of the receptor and also includes directly or indirectly affecting the normal regulation of the receptor activity. Compounds which modulate the receptor activity include agonists, antagonists and compounds which directly or indirectly affect regulation of the receptor activity.

The prostaglandin receptor of the present invention may be obtained from both native and recombinant sources for use in an assay procedure to identify receptor modulators. In general, an assay procedure to identify prostaglandin receptor modulators will contain the prostaglandin receptor of the present invention, and a test compound or sample which contains a putative prostaglandin receptor modulator. The test compounds or samples may be tested directly on, for example, purified receptor protein whether native or recombinant, subcellular fractions of receptor-producing cells whether native or recombinant, and/or whole cells expressing the receptor whether native or recombinant. The test compound or sample may be added to the receptor in the presence or absence of a known labelled or unlabelled receptor ligand. The modulating activity of the test compound or sample may be determined by, for example, analyzing the ability of the test compound or sample to bind to the receptor, activate the receptor, inhibit receptor activity, inhibit or enhance the binding of other compounds to the receptor, modify receptor regulation, or modify an intracellular activity.

The identification of modulators of FP receptor activity are useful in treating disease states involving the FP receptor activity. Other compounds may be useful for stimulating or inhibiting activity of the receptor. Selective agonists of the FP receptor may be of use in the treatment of glucoma through their ability to lower intraocular pressure and may have utility in the synchronization of oestrus cycles in farm animals through their ability to stimulate luteolytic function. Compounds which antagonize the FP receptor could be of use in the treatment of diseases in which activation of the FP receptor results in either cellular proliferation, induction of cellular neoplastic trasnsformations or metastatic tumor growth or pathological states where activation of the FP receptor causes smooth muscle contraction such as the uterine contractions observed in dysmenorrhea. The isolation and purification of an FP-encoding DNA molecule would be useful for establishing the tissue distribution of FP receptors, studying changes in FP receptor expression in disease states, as well as establishing a process for identifying compounds which modulate FP receptor activity.

The following examples are provided for the purpose of illustrating the present invention without, however, limiting the same thereto.

EXAMPLE 1
Cloning of the FP cDNA

An antisense 16-fold degenerate 27 mer oligonucleotide [5'-ATA(A,C)ACCCAGGG(A,G)TCCA(A,G)GATCTG(G,A)TT-3'] (SEQ.ID.NO.:1) based on the 9 conserved amino acids (NQILDPWVY) (SEQ.ID.NO.:2) in transmembrane domain VII was synthesized. The $^{32}$P-labeled oligo probe was initially used to screen a mouse kidney lambda gt10 library (Clontech, Palo Alto, Calif.) using standard techniques (Sambrook et al., 1989. Molecular Cloning: A Laboratory Manual, 2nd Ed., Cold Spring Harbor Laboratory, Cold Spring Harbor, N.Y.). A putative mouse FP partial cDNA (430 bp) was cloned and sequenced. PCR was then used to generate a 373 bp cDNA probe (see below), based on the mouse sequence, to be used to screen a human kidney lambda gt11 library (Clontech, Palo Alto, Calif.).

The sequence of the 373 bp PCR generated probe from a putative mouse FP partial cDNA clone is as follows:

CTCTTAGCTCTTGGTGTTTCCTTCTCGTGCAATGCCGTCACGGGAGTCAC
ACTCTTAAGAGTGAAGTTCAGAAGCCAGCAGCATAGGCAAGGCAGATCT
CACCACCTGGAGATGATCATTCAGCTCCTGGCCATAATGTGCGTCTCCTG
CGTCTGCTGGAGTCCCTTTCTGGTAACAATGGCCAACATTGCAATAAATG
GAAATAATTCCCCAGTGACCTGTGAAACGACACTTTTTGCTCTCCGCATG
GCAACGTGGAATCAGATCTTAGATCCCTGGGTCTATATTCTGCTACGGAA
GGCTGTCCTTAGGAACCTGTATAAACTTGCCAGTCGTTGCTGTGGAGTTA
ACATCATCAGCTTGCATATCTGGG (SEQ.ID.NO.: 3).

In this manner, two partial length human FP cDNA clones were obtained of approx. 1.7 and 1.8 kb in length. A 1 kb EcoRI 5' fragment from one of the clones was purified, $^{32}$P-labeled and subsequently used to probe a human uterus lambda gt10 library (Clontech, Palo Alto, Calif.). From this screening a 2.8 kb cDNA clone was plaque-purified and DNA was prepared by the plate lysate method (Sambrook et al., 1989. Molecular Cloning: A Laboratory Manual, 2nd Ed., Cold Spring Harbor Laboratory, Cold Spring Harbor, N.Y.).

Subcloning and sequencing of cDNA

The 2.5 kb cDNA clone was digested with EcoRI and was found to contain two inserts of sizes 1.8 kb and 0.7 kb . Only the 1.8 kb insert was found to hybridize with the human receptor partial cDNA probe upon Southern blot analysis. The 1.8 kb EcoRI fragment (FP) was subcloned into pKS vector (Stratagene, La Jolla, Calif.) for sequencing using the T7 DNA polymerase sequencing kit (Pharmacia). The DNA was sequenced entirely on both strands using the KS and SK primers (Stratagene, La Jolla, Calif.) or primers generated from the determined sequence. The nucleotide sequence of FP is shown in Table 1. The amino acid sequence for the encoded protein is shown in Table 2. The 1.8 kb fragment (FP; FIG. 1), when sequenced, was found to contain sequence homology to the human thromboxane receptor cDNA and the putative heptahelical arrangement characteristic of G protein-coupled receptors was evident. A long open reading frame (1077 bp) was determined which would result in a 359 amino acid polypeptide with a predicted relative molecular mass of 40,060. The ATG assigned as the initiator codon matches the Kozak consensus sequence for translation initiation (Kozak, 1989 J. Cell. Biol., 108, pp 229–241). The FP cDNA contains a long 3' untranslated region of about 1200 base pairs.

EXAMPLE 2
Construction of pcDNAIamp-FP expression vector

The 1.8 Kb EcoRI human FP cDNA fragment was subcloned into the EcoRI site of pcDNAIamp and the correct orientation was verified by Pst I digestion.

TABLE 1

```
GTGCGCGGAGGGGACGAGCGGGTGGACCACAGCCGGCGCCCGATCAGGATCTCCGCG
CTGGGATCGGTGGAACTTGAGGCAGCGGCGGCGCGGGGCGCCATGGCACACCGAGCG
GCTCCGTCTTCTGCTCCTCAGAGAGCCCGGCTGGCGGCCTGGGATGACAAGATGTCT
GGACTGCAATCCTGCACAGTTTTGAGAGGGAGATGACTTGAGTGGTTGGCTTTTATC
TCCACAACAATGTCCATGAACAATTCCAAACAGCTAGTGTCTCCTGCAGCTGCGCTT
CTTTCAAACACAACCTGCCAGACGGAAAACCGGCTTTCCGTATTTTTTTCAGTAATC
TTCATGACAGTGGGAATCTTGTCAAACAGCCTTGCCATGGCCATTCTCATGAAGGCA
TATCAGAGATTTAGACAGAAGTCCAAGGCATCGTTTCTGCTTTTGGCCAGCGGCCTG
GTAATCACTGATTTCTTTGGCCATCTCATCAATGGAGCCATAGCAGTATTTGTATAT
GCTTCTGATAAAGAATGGATCCGCTTTGACCAATCAAATGTCCTTTGCAGTATTTTT
GGTATCTGCATGGTGTTTCTGGTCTGTGCCCACTTCTTCTAGGCAGTGTGATGGCC
ATTGAGCGGTGTATTGGAGTCACAAAACCAATATTTCATTCTACGAAAATTACATCC
AAACATGTGAAAATGATGTTAAGTGGTGTGTGCTTGTTTGCTGTTTTCATAGCTTTG
CTGCCCATCCTTGGACATCGAGACTATAAAATTCAGGCGTCGAGGACCTGGTGTTTC
TACAACACAGAAGACATCAAAGACTGGGAAGATAGATTTTATCTTCTACTTTTTTCT
TTTCTGGGGCTCTTAGCCCTTGGTGTTTCATTGTTGTGCAATGCAATCACAGGAATT
ACACTTTTAAGAGTTAAATTTAAAAGTCAGCAGCACAGACAAGGCAGATCTCATCAT
TTGGAAATGGTAATCCAGCTCCTGGCGATAATGTGTGTCTCCTGTATTTGTTGGAGC
CCATTTCTGGTTACAATGGCCAACATTGGAATAAATGGAAATCATTQTCTGGAAACC
TGTGAAACAACACTTTTTGCTCTCCGAATGGCAACATGGAATCAAATCTTAGATCCT
TGGGTATATATTCTTCTACGAAAGGCTGTCCTTAAGAATCTCTATAAGCTTGCCAGT
CAATGCTGTGGAGTGCATGTCATCAGCTTACATATTTGGGAGCTTAGTTCCATTAAA
AATTCCTTAAAGGTTGCTGCTATTTCTGAGTCACCAGTTGCAGAGAAATCAGCAAGC
ACCTAGCTTAATAGGACAGTAAATCTGTGTGGGGCTAGAACAAAAATTAAGACATGT
TTGGCAATATTTCAGTTAGTTAAATACCTGTAGCCTAACTGGAAAATTCAGGCTTCA
TCATGTAGTTTG (SEQ.ID.NO.:4)
```

TABLE 2

```
MSMNNSKQLVSPAAALLSNTTCQTENRLSVFFSVIFMTVGILSNSLAIAILMKAYQR
FRQKSKASFLLLASGLVITDFFGHLINGAIAVFVYASDKEWIRFDQSNVLCSIFGIC
MVFSGLCPLLLGSVMAIERCIGVTKPIFHSTKITSKHVKMMLSGV6LFAVFIALLPI
LGHRDYKIQASRTWCFYNTEDIKDWEDRFYLLLFSFLGLLALGVSLLCNAITGITLL
RVKFKSQQHRQGRSHHLEMVIQLLAIMCVSCICWSPFLVTMANIGINGNHSLETCET
TLFALRMATWNQILDPWVYILLRKAVLKNLYKLASQCCGVHVISLHIWELSSIKNSL
KVAAISESPVAEKSAST (SEQ.ID.NO.:5)
```

EXAMPLE 3
Cloning of the FP cDNA into *E. coli* Expression Vectors

Recombinant FP is produced in *E. coli* following the transfer of the FP expression cassette into *E. coli* expression vectors, including but not limited to, the pET series (Novagen). The pET vectors place FP expression under control of the tightly regulated bacteriophage T7 promoter. Following transfer of this construct into an *E. coli* host which contains a chromosomal copy of the T7 RNA polymerase gene driven by the inducible lac promoter, expression of FP is induced when an appropriate lac substrate (IPTG) is added to the culture. The levels of expressed FP are determined by the assays described above.

The cDNA encoding the entire open reading frame for FP is inserted into the NdeI site of pET 11*a*. Constructs in the positive orientation are identified by sequence analysis and used to transform the expression host strain BL21. Transformants are then used to inoculate cultures for the production of FP protein. Cultures may be grown in M9 or ZB media, whose formulation is known to those skilled in the art. After growth to an approximate $OD_{600}=1.5$, expression of FP is induced with 1 mM IPTG for 3 hours at 37° C. FP receptor binding activity will be found in membrane fractions from these cells.

EXAMPLE 4
In Vivo Translation of Synthetic FP mRNA by Xenopus Oocyte Microinjection and Expression in Mammalian Cells FP cDNA constructs are ligated into in vitro transcription vectors (the pGEM series, Promega) for the production of synthetic mRNAs.

Synthetic MRNA is produced in sufficient quantity in vitro by cloning double stranded DNA encoding FP MRNA into a plasmid vector containing a bacteriophage promoter, linearizing the plasmid vector containing the cloned FP-encoding DNA, and transcribing the cloned DNA in vitro using a DNA-dependent RNA polymerase from a bacteriophage that specifically recognizes the bacteriophage promoter on the plasmid vector.

Various plasmid vectors are available containing a bacteriophage promoter recognized by a bacteriophage DNA-dependent RNA polymerase, including but not limited to plasmids pSP64, pSP65, pSP70, pSP71, pSP72, pSP73, pGEM-3Z, pGEM-4Z, pGEM-3Zf, pGEM-5Zf, pGEM-7Zf, pGEM-9Zf, and pGEM-11Zf, the entire series of plasmids is commercially available from Promega.

The double stranded FP-encoding DNA is cloned into the bacteriophage promoter containing vector in the proper orientation using one or more of the available restriction endonuclease cloning sites on the vector which are convenient and appropriate for cloning FP DNA. The vector with the ligated FP DNA is used to transform bacteria, and clonal isolates are analyzed for the presence of the vector with the FP DNA in the proper orientation.

Once a vector containing the FP-encoding DNA in the proper orientation is identified and isolated, it is linearized by cleavage with a restriction endonuclease at a site downstream from, and without disrupting, the FP transcription unit. The linearized plasmid is isolated and purified, and used as a template for in vitro transcription of FP mRNA.

The template DNA is then mixed with bacteriophage-specific DNA-dependent RNA polymerase in a reaction mixture which allows transcription of the DNA template forming FP mRNA. Several bacteriophage-specific DNA-dependent RNA polymerases are available, including but not limited to T3, T7, and SP6 RNA polymerase. The synthetic FP mRNA is then isolated and purified.

It may be advantageous to synthesize mRNA containing a 5' terminal cap structure and a 3' poly A tail to improve mRNA stability. A cap structure, or 7-methylguanosine, may be incorporated at the 5' terminus of the niRNA by simply adding 7-methylguanosine to the reaction mixture with the DNA template. The DNA-dependent RNA polymerase incorporates the cap structure at the 5' terminus as it synthesizes the mRNA. The poly A tail is found naturally occurring in many cDNAs but can be added to the 3' terminus of the mRNA by simply inserting a poly A tail-encoding DNA sequence at the 3' end of the DNA template.

The isolated and purified FP MRNA is translated using either a cell-free system, including but not limited to rabbit reticulocyte lysate and wheat germ extracts (both commercially available from Promega and New England Nuclear) or in a cell based system, including but not limited to microinjection into Xenopus oocytes, with microinjection into Xenopus oocytes being preferred.

Xenopus oocytes are microinjected with a sufficient amount of synthetic FP mRNA to produce FP protein. The microinjected oocytes are incubated to allow translation of the FP mRNA, forming FP protein.

These synthetic mRNAs are injected into Xenopus oocytes (stage 5–6) by standard procedures [Gurdon, J. B. and Wickens, M. D. Methods in Enzymol. 101: 370–386, (1983)]. Oocytes are harvested and analyzed for FP expression as described below.

EXAMPLE 5
pcDNAIamp-FP expression in Xenopus oocytes

Ooctyes were taken from adult females of *Xenopus laevis* using standard surgical procedure (Colman, A., 1984 In: Transcription and Translation—A Practical Approach, IRL Press). To remove follicle cells, oocytes were treated for 2–3 h with freshly made collagenase (2 mg/ml, type 2, Worthington Biochemical Corp., Freehold, N.J.) in $Ca^{2+}$-free ND96 solution (ND96 in mM: NaCl 96, KCl 2, $MgCl_2$ 1, HEPES 5, Na-pyruvate 2.5, theophylline 0.5, gentamicin 50 mg/ml, +1.8 $CaCl_2$, pH 7.6). Defolliculated stage 5–6 oocytes were selected and maintained in ND96 solution. Ooctye nuclei were injected with 1–5 ng of pcDNAIamp-FP and then incubated at 18° C. for 48 h before challenge with agonist. Functional activity was determined by measurement of either agonist-induced $Ca^{2+}$-dependent C1-current or light emission in oocytes injected with the $Ca^{2+}$-specific photoprotein aequorin (J. Blinks, Friday Harbor Photoproteins, Wash.), (Giladi and Spindel 1991 Biotechniques, 10, pp 744–747). For the electrophysiological assays an ooctye was placed in a 0.5 ml perfusion chamber and voltage clamped at −60 mV (with microelectrodes of 0.5–2.0 MW resistance filled with 3M KCl) using a Turbo TEC 01C amplifier (NPl Instruments, Germany). Ligand-containing solution was perfused and the current response was recorded. For the luminometric assay, aequorin-loaded oocytes (100 ng/oocyte) were placed individually in cuvettes containing 0.4 ml ND96 and the light emission provoked by ligand addition was recorded using a Bio-Orbit 1251 luminometer (Fisher Sci. Ltd.).

Figure 3B:
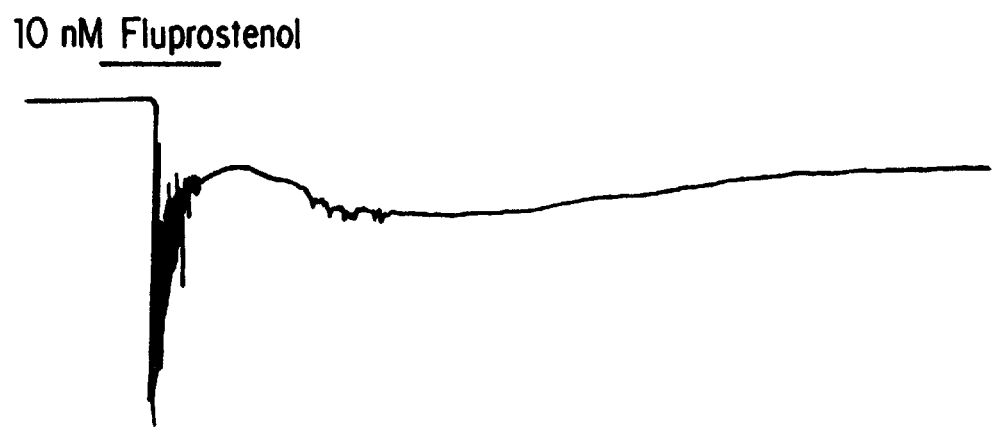
Figure 4A:
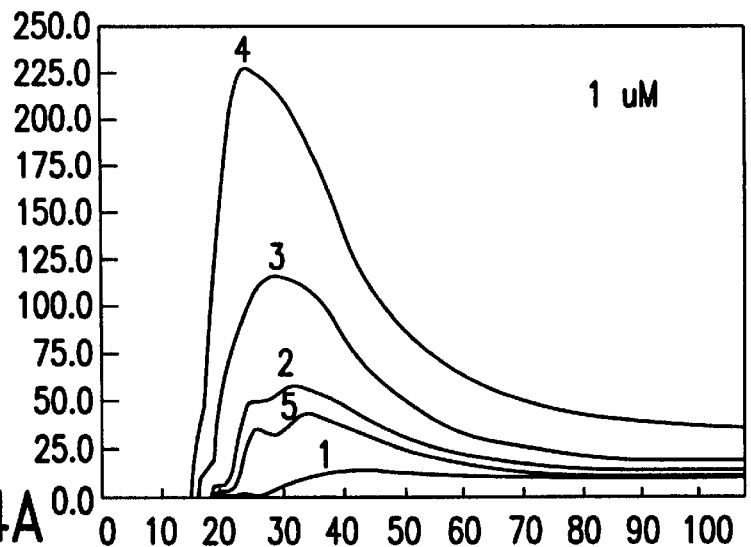
FIGS. 4A, 4B and 4C - $PGF_{2\alpha}$-induced light responses in aequorin loaded oocytes expressing recombinant FP receptor. Superimposed individual responses of 5 oocytes tested at each $PGF_{2\alpha}$ concentration (1 µM—FIG. 4A; 100 nm—FIG. 4B; and 10 nM—FIG. 4C). The ligand was added into the recording cuvette at 10 s; the aequorin light emission is expressed in relative units with the background emission being typically 0.5–0.7 units.
Figure 4B:
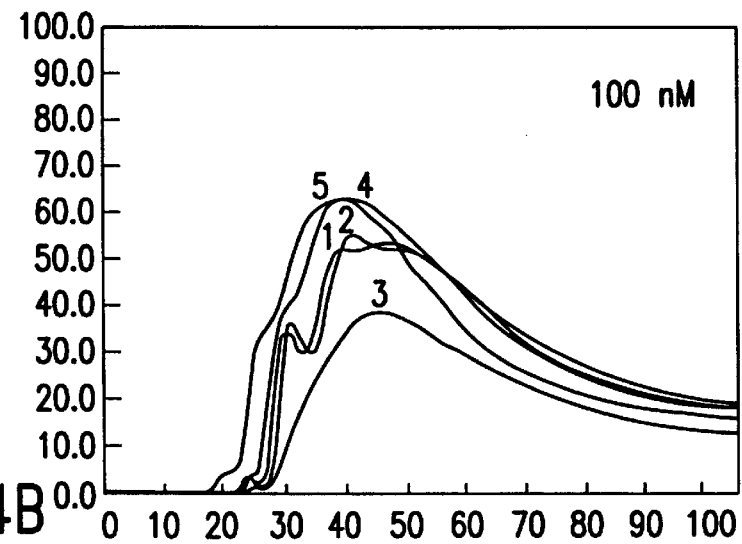
Figure 4C:
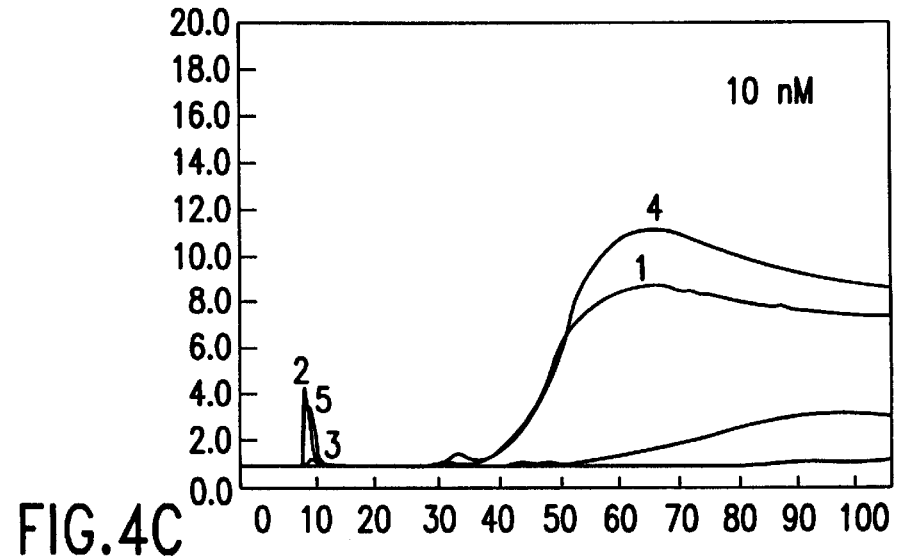
Figure 5:
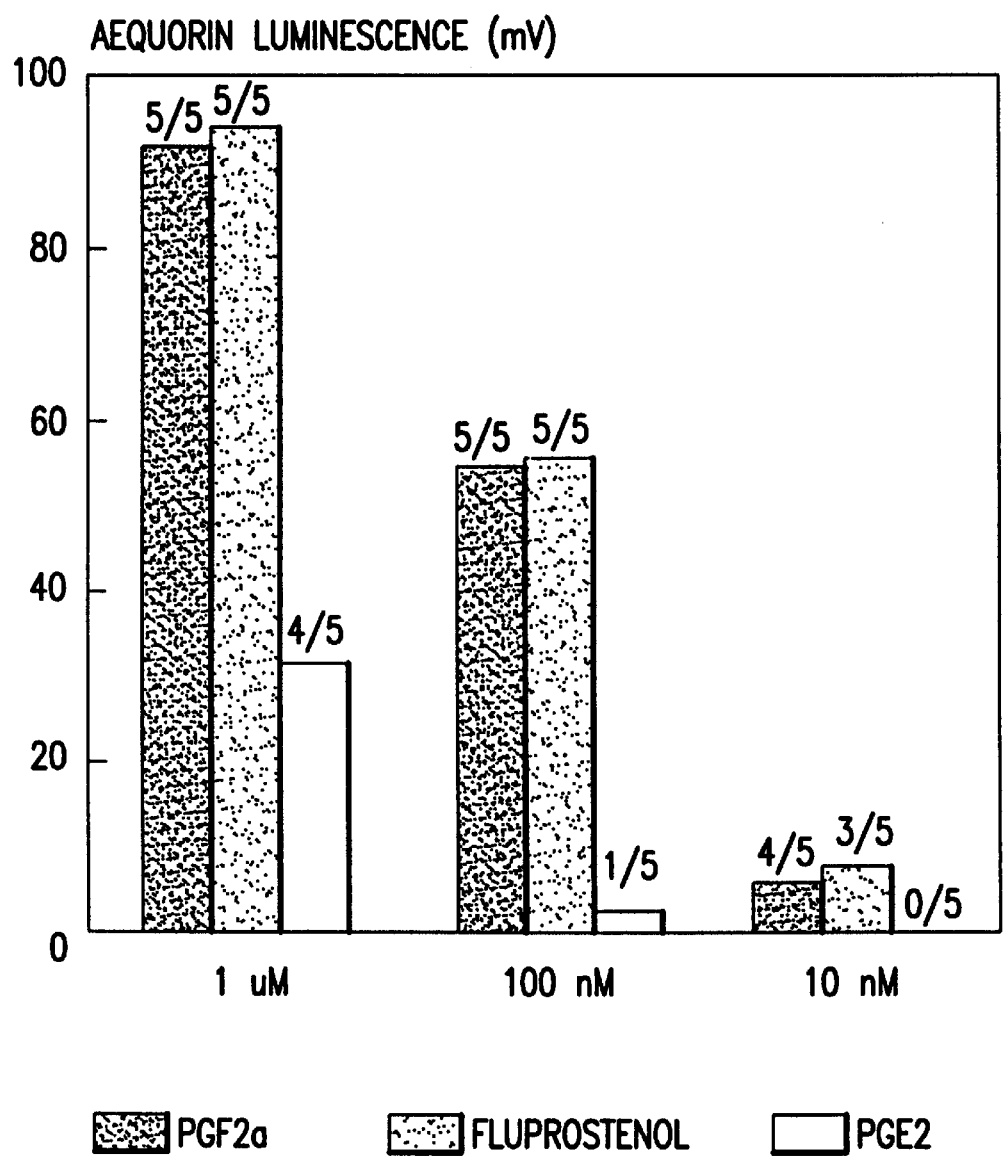
FIG. 5 - Average light responses evoked by different concentrations of $PGF_{2\alpha}$, fluprostenol and $PGE_2$. Each bar represents average response from 5 oocytes obtained from the same donor and the numbers above each bar indicate the number of oocytes responding. Similar results were obtained with oocytes from 5 other donors.
Figure 6:
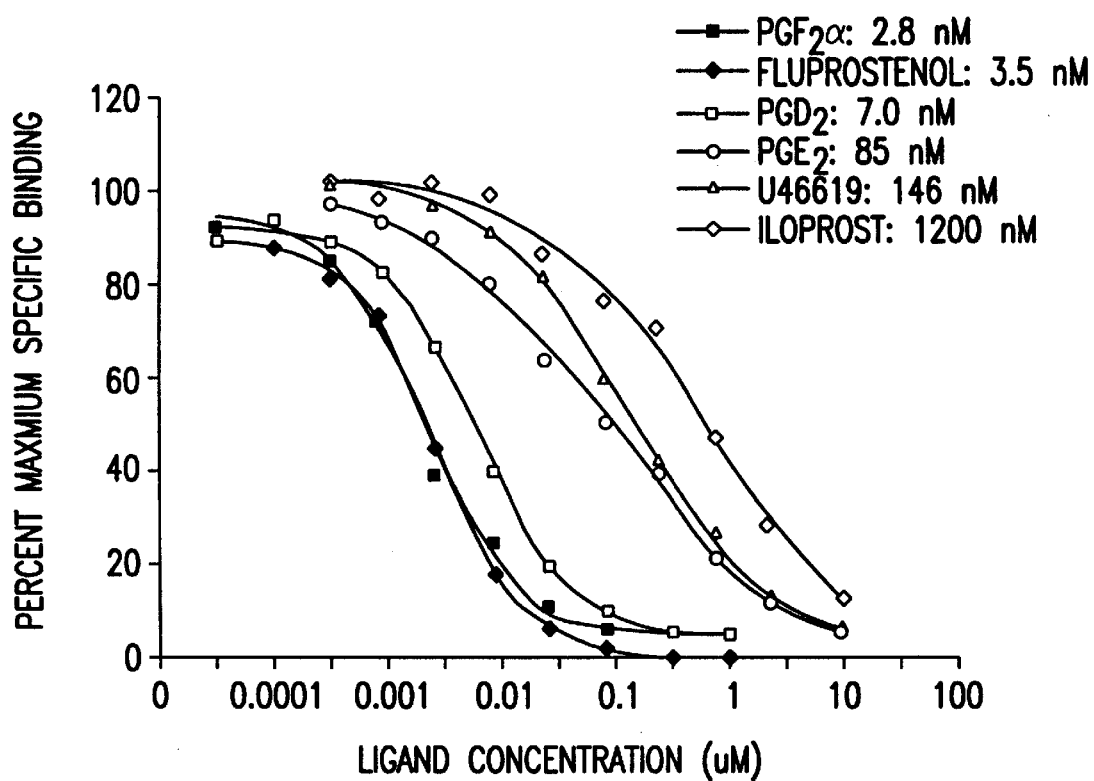
FIG. 6 - Competition for [3H]$PGF_{2\alpha}$ specific binding to pcDNAIamp-hFP transfected COS-M6 membranes. [3H]$PGF_{2\alpha}$ binding assays were performed as described in the Methods in the presence of 0.03 nM-10 µM $PGF_{2\alpha}$ (■), fluprostenol (●), $PGD_2$ (□), $PGE_2$ (○), U46619 (∆) and iloprost (◇).

Functional activity was determined in pcDNAIamp-FP-injected oocytes using electrophysiological and aequorin luminescence assays. In the electrophysiological assay, perfusion of 10 to 20 nM $PGF_{2\alpha}$ or 10 nM fluprostenol, a selective FP receptor agonist, resulted in prominent current responses in oocytes injected with pcDNAIamp-FP confirming that this clone encodes a functional FP receptor that is coupled to the phosphatidylinositol/$Ca^{2+}$ signalling pathway (FIG. 3A and 3B). Such responses were absent in control ($H_2O$-injected) oocytes. Ligand-induced increases in intracellular $Ca^{2+}$ were also, demonstrated directly by light emission in aequorin-loaded oocytes (FIG. 4A, 4B and 4C,. The dose-response dependencies obtained from aequorin lunmnescence assay indicated that $PGF_{2\alpha}$ and fluprostenol were more potent agonists of the expressed receptor when compared to $PGE_2$ (FIG. 5). This rank order of potency is consistent with that reported for the FP receptor [Coleman, et al., 1991].

EXAMPLE 6
Cloning of FP cDNA into a Mammalian Expression Vector

FP cDNA expression cassettes are ligated at appropriate restriction endonuclease sites to the following vectors containing strong, universal mammalian promoters: pBC12BI [Cullen, B. R. Methods in Enzymol. 152: 684–704 1988], and pEE12 (CellTech EP 0 338,841) and its derivatives pSZ9016-1 and p9019. p9019 represents the construction of a mammalian expression vector containing the hCMVIE promoter, polylinker and SV40 polyA element with a selectable marker/amplification system comprised of a mutant gene for dihydrofolate reductase (mDHFR) (Simonsen, C. C. and Levinson, A. D. Proc. Natl. Acad. Sci USA 80: 2495–2499 [1983]) driven by the SV40 early promoter. An SV40 polyadenylation sequence is generated by a PCR reaction defined by primers 13978-120 and 139778-121 using pD5 (Berker and Sharp, Nudl. Acid Res. 13: 841–857 [1985]) as template. The resulting 0.25 Kb PCR product is digested with ClaI and SpeI and ligated into the 6.7 Kb fragment of pEE12 which had been likewise digested. The resultant plasmid is digested with BglII and SfiI to liberate the 3' portion of the SV40 early promoter and the GScDNA from the vector. A 0.73 Kb SfiI-XhoII fragment isolated from plasmid pFR400 (Simonsen, C. C. and Levinson, A. D. Proc. Natl. Acad. Sci USA 80: 2495–2499 [1983]) is ligated to the 5.6 Kb vector described above, reconstituting the SV40 early promoter, and inserting the mdHF gene. This plasmid is designated p9019. pSZ9016-1 is identical to p9019 except for the substitution of the HIV LTR for the huCMVIE promoter. This vector is constructed by digesting p9019 with XbaI and MluI to remove the huCMVIE promoter. The HIV LTR promoter, from residue −117 to +80 (as found in the vector pCD23 containing the portion of the HIV-1 LTR (Cullen, Cell 46:973 [1986]) is PCR amplified from the plasmid pCD23 using oligonucleotide primers which appended to the ends of the product the MluI and SpeI restriction sites on the 5' side while Hind III and Xba I sites are appended on the 3' side. Following the digestion of the resulting 0.2 kb PCR product with the enzymes MluI and Xba I the fragment is agarose gel-purified and ligated into the 4.3 Kb promoterless DNA fragment to generate the vector pSZ9016-1.

Cassettes containing the FP cDNA in the positive orientation with respect to the promoter are ligated into appropriate restriction sites 3' of the promoter and identified by restriction site mapping and/or sequencing. These cDNA expression vectors are introduced into various host cells including, but not limited to: COS-7 (ATCC# CRL1651), CV-1 [Sackevitz et al., Science 238:1575 (1987)], 293, L cells (ATCC# CRL6362)] by standard methods including but not limited to electroporation,or chemical procedures (cationic liposomes, DEAE dextran, calcium phosphate). Transfected cells and cell culture extracts can be harvested and analyzed for FP expression as described below.

All of the vectors used for mammalian transient expression can be used to establish stable cell lines expressing FP. Unaltered FP cDNA constructs cloned into expression vectors will be expected to program host cells to make intracellular FP protein. The transfection host cells include, but are not limited to, CV-1 [Sackevitz et al., Science 238: 1575 (1987)], tk-L [Wigler, et al. Cell 11: 223 (1977)], NS/O, and dHFr-CHO [Kaufman and Sharp, J. Mol. Biol. 159: 601, (1982)].

Co-transfection of any vector containing FP cDNA with a drug selection plasmid including, but not limited to G418, aminoglycoside phosphotransferase, pLNCX [Miller, A. D. and Rosman G. J. Biotech News 7: 980–990 (1989)]; hygromycin, hygromycin-B phosphotransferase, pLG90 [Gritz. L. and Davies, J., GENE 25: 179 (1983)]; APRT, xanthine-guanine phosphoribosyl-transferase, pMAM (Clontech) [Murray, et al., Gene 31: 233 (1984)] will allow for the selection of stably transfected clones. Levels of FP are quantitated by the assays described above.

FP cDNA constructs are ligated into vectors containing amplifiable drug-resistance markers for the production of mammalian cell clones synthesizing the highest possible levels of FP. Following introduction of these constructs into cells, clones containing the plasmid are selected with the appropriate agent, and isolation of an overexpressing clone with a high copy number of the plasmid is accomplished by selection in increasing doses of the agent. The following systems are utilized: the 9016 or the 9019 plasmid containing the mutant DHFR gene [Simonson, C. and Levinson, A., Proc. Natl. Acad. Sci. USA 80: 2495 (1983)], transfected into DHFR- CHO cells and selected in methotrexate; the pEE12 plasmid containing the glutamine synthetase gene, transfected into NS/O cells and selected in methionine sulfoximine (CellTech International Patent Application 2089/10404); and 9016 or other CMV promoter vectors, co-transfected with pDLAT-3 containing the thymidine kinase gene [Colbere and Garopin, F., Proc. Natl. Acad. Sci. 76: 3755 (1979)] in APRT and TK deficient L cells, selected in APRT (0.05 mM azaserine, 0.1 mM adenine, 4 ug/ml adenosine) and amplified with HAT (100 uM hypoxanthine, 0.4 uM aminopterin, 16 uM thymidine).

EXAMPLE 7
Expression of the FP receptor in COS-M6 cells and [3H] PGF$_{2\alpha}$ binding assays The recently cloned human prostaglandin F$_{2\alpha}$ (FP) receptor was subcloned into the pcDNA lamp plasmid (Invitrogen) and transfected into COS-M6 cells using the DEAE-dextran method. The cells were maintained in culture for 72 h, then harvested and membranes prepared by differential centrifugation (1000× g for 10 min, then 100,000× g for 30 min) following lysis of the cells by nitrogen cavitation. [3H]Prostaglandin F$_{2\alpha}$ ([3H]PGF$_{2\alpha}$) binding assays were performed in 10 mM MES/KOH pH 6.0, containing 0.4 mM EDTA, 10 mM MnCl$_2$, 0.3 nM [3H] PGF$_{2\alpha}$ and 60 μg of protein from the 100,000× g membrane fraction. Incubations were conducted for 1 h at room temperature prior to separation of the bound and free radioligand by rapid filtration through Whatman GF/B filters presoaked at 4° C. in washing buffer (10 μM MES/KOH (pH 6.0) containing 0.01% bovine serum albumin). The filters were washed with approximately 16 ml of washing buffer and the residual [3H]PGF$_{2\alpha}$ bound to the filter was quantified by liquid scintillation counting. Specific binding was defined as the difference between total binding and nonspecific binding, determined in the presence of 2 μM PGF$_{2\alpha}$.

The cloned human FP receptor was transfected into COS-M6 cells and [3H]PGF$_{2\alpha}$ binding assays were performed with membranes prepared from the transfected cells. In competition assays PGF$_{2\alpha}$ was the most potent competing ligand for [3H]PGF$_{2\alpha}$ specific binding with an IC50 value of 2.8 nM (FIG. X). The related synthetic FP agonist fluprostenol was equipotent with an IC50 value of 3.5 nM. The rank order of potency for prostaglandins and related analogs was: PGF$_{2\alpha}$=fluprostenol>PGD$_2$>>PGE$_2$≈U46619>iloprost. U46619 and iloprost are stable analogs of thromboxane and prostacyclin and display comparable potency at the TP and IP receptors, respectively. This rank order of potency has been predicted for the FP receptor from previous pharmacological studies.

EXAMPLE 8
Cloning of FP cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL#1711). Recombinant baculoviruses expressing FP cDNA are produced by the following standard methods (InVitrogen Maxbac Manual): the FP cDNA constructs are ligated downstream of the polyhedrin promoter in a variety of baculovirus transfer vectors, including the pAC360 and the pBlueBac vector (InVitrogen). Recombinant baculoviruses are generated by homologous recombination following co-transfection of the baculovirus transfer vector and linearized AcNPV genomic DNA [Kitts, P. A., Nuc. Acid. Res. 18: 5667 (1990)] into Sf9 cells. Recombinant pAC360 viruses are identified by the absence of inclusion bodies in infected cells (Summers, M. D. and Smith, G. E., Texas Agriculture Exp. Station Bulletin No. 1555) and recombinant pBlueBac viruses are identified on the basis of b-galactosidase expression (Vialard, et al. 1990, J. Virol., 64, pp 37–50). Following plaque purification and infection of sf9 cells with FP recombinant baculovirus, FP expression is measured by the assays described above.

The cDNA encoding the entire open reading frame for FP is inserted into the BamHiI site of pBlueBacII. Constructs in the positive orientation with respect to the polyhedrin promoter are identified by sequence analysis and used to transfect Sf9 cells in the presence of linear AcNPV wild type DNA.

Authentic, active FP is found associated with the membranes of infected cells. Membrane preparations are prepared from infected cells by standard procedures.

EXAMPLE 9
Cloning of FP cDNA into a yeast expression vector

Recombinant FP is produced in the yeast S. cerevisiae following the insertion of the optimal FP cDNA construct into expression vectors designed to direct the intracellular expression of heterologous proteins. For intracellular expression, vectors such as EmBLyex4 or the like are ligated to the FP cistron [Rinas, U. et al., Biotechnology 8: 543–545 (1990); Horowitz B. et al., J. Biol. Chem. 265: 4189–4192 (1989)]. The levels of expressed FP are determined by the assays described above.

EXAMPLE 10
Purification of Recombinant FP

Recombinantly produced FP may be purified by antibody affinity chromatography.

FP antibody affinity columns are made by adding the anti-FP antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatants or cell extracts containing solubilized FP or FP subunits are slowly passed through the column. The column is then washed with phosphate-buffered saline together with detergents until the optical density (A280) falls to background, then the protein is eluted with 0.23M glycine-HCl (pH 2.6) together with detergents. The purified FP protein is then dialyzed against phosphate buffered saline together with detergents.

What is claimed is:

1. An isolated and purified DNA molecule encoding a human FP prostaglandin receptor protein wherein said protein comprises the amino acid sequence as set forth in SEQ.ID. NO.:5.

2. An isolated and purified DNA molecule encoding a human prostaglandin FP receptor protein where said DNA molecule comprises the nucleotide sequence as set for in SEQ. ID. NO.:4.

3. An expression vector for the expression of a human prostaglandin FP receptor protein in a recombinant host cell wherein said expression vector contains the DNA molecule of claim 2.

4. A host cell which expresses a recombinant human prostaglandin FP receptor protein wherein said host cell contains the expression vector of claim 3.

5. A process for the expression of a human prostaglandin EP receptor protein in a recombinant host cell, comprising:

(a) transfecting the expression vector of claim 3 into a suitable host cell; and (b) culturing the host cells under conditions which allow expression of the prostaglandin receptor protein from the expression vectors.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:1:

ATAMACCCAG GGRTCCARGA TCTGRTT                                                                               2 7

( 2 ) INFORMATION FOR SEQ ID NO:2:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:2:

Asn  Gln  Ile  Leu  Asp  Pro  Trp  Val  Tyr
    1              5

( 2 ) INFORMATION FOR SEQ ID NO:3:

( i ) SEQUENCE CHARACTERISTICS:
    ( A ) LENGTH: 373 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:3:

CTCTTAGCTC TTGGTGTTTC CTTCTCGTGC AATGCCGTCA CGGGAGTCAC ACTCTTAAGA      6 0

GTGAAGTTCA GAAGCCAGCA GCATAGGCAA GGCAGATCTC ACCACCTGGA GATGATCATT    1 2 0

CAGCTCCTGG CCATAATGTG CGTCTCCTGC GTCTGCTGGA GTCCCTTTCT GGTAACAATG    1 8 0

GCCAACATTG CAATAAATGG AAATAATTCC CCAGTGACCT GTGAAACGAC ACTTTTTGCT    2 4 0

CTCCGCATGG CAACGTGGAA TCAGATCTTA GATCCCTGGG TCTATATTCT GCTACGGAAG    3 0 0

GCTGTCCTTA GGAACCTGTA TAAACTTGCC AGTCGTTGCT GTGGAGTTAA CATCATCAGC    3 6 0

TTGCATATCT GGG                                                                                              3 7 3

( 2 ) INFORMATION FOR SEQ ID NO:4:

( i ) SEQUENCE CHARACTERISTICS:

(A) LENGTH: 1437 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:4:

| | | | | | | |
|---|---|---|---|---|---|---|
| GTGCGCGGAG | GGGACGAGCG | GCTGGACCAC | AGCCGGCGCC | CGATCAGGAT | CTCCGCGCTG | 60 |
| GGATCGGTGG | AACTTGAGGC | AGCGGCGGCG | CGGGGCGCCA | TGGCACACCG | AGCGGCTCCG | 120 |
| TCTTCTGCTC | CTCAGAGAGC | CCGGCTGGCG | GCCTGGGATG | ACAAGATGTC | TGGACTGCAA | 180 |
| TCCTGCACAG | TTTTGAGAGG | GAGATGACTT | GAGTGGTTGG | CTTTTATCTC | CACAACAATG | 240 |
| TCCATGAACA | ATTCCAAACA | GCTAGTGTCT | CCTGCAGCTG | CGCTTCTTTC | AAACACAACC | 300 |
| TGCCAGACGG | AAAACCGGCT | TTCCGTATTT | TTTTCAGTAA | TCTTCATGAC | AGTGGGAATC | 360 |
| TTGTCAAACA | GCCTTGCCAT | CGCCATTCTC | ATGAAGGCAT | ATCAGAGATT | TAGACAGAAG | 420 |
| TCCAAGGCAT | CGTTTCTGCT | TTTGGCCAGC | GGCCTGGTAA | TCACTGATTT | CTTTGGCCAT | 480 |
| CTCATCAATG | GAGCCATAGC | AGTATTTGTA | TATGCTTCTG | ATAAAGAATG | GATCCGCTTT | 540 |
| GACCAATCAA | ATGTCCTTTG | CAGTATTTTT | GGTATCTGCA | TGGTGTTTTC | TGGTCTGTGC | 600 |
| CCACTTCTTC | TAGGCAGTGT | GATGGCCATT | GAGCGGTGTA | TTGGAGTCAC | AAAACCAATA | 660 |
| TTTCATTCTA | CGAAAATTAC | ATCCAAACAT | GTGAAAATGA | TGTTAAGTGG | TGTGTGCTTG | 720 |
| TTTGCTGTTT | TCATAGCTTT | GCTGCCCATC | CTTGGACATC | GAGACTATAA | AATTCAGGCG | 780 |
| TCGAGGACCT | GGTGTTTCTA | CAACACAGAA | GACATCAAAG | ACTGGGAAGA | TAGATTTTAT | 840 |
| CTTCTACTTT | TTTCTTTTCT | GGGGCTCTTA | GCCCTTGGTG | TTTCATTGTT | GTGCAATGCA | 900 |
| ATCACAGGAA | TTACACTTTT | AAGAGTTAAA | TTTAAAAGTC | AGCAGCACAG | ACAAGGCAGA | 960 |
| TCTCATCATT | TGGAAATGGT | AATCCAGCTC | CTGGCGATAA | TGTGTGTCTC | CTGTATTTGT | 1020 |
| TGGAGCCCAT | TTCTGGTTAC | AATGGCCAAC | ATTGGAATAA | ATGGAAATCA | TTCTCTGGAA | 1080 |
| ACCTGTGAAA | CAACACTTTT | TGCTCTCCGA | ATGGCAACAT | GGAATCAAAT | CTTAGATCCT | 1140 |
| TGGGTATATA | TTCTTCTACG | AAAGGCTGTC | CTTAAGAATC | TCTATAAGCT | TGCCAGTCAA | 1200 |
| TGCTGTGGAG | TGCATGTCAT | CAGCTTACAT | ATTTGGGAGC | TTAGTTCCAT | TAAAAATTCC | 1260 |
| TTAAAGGTTG | CTGCTATTTC | TGAGTCACCA | GTTGCAGAGA | AATCAGCAAG | CACCTAGCTT | 1320 |
| AATAGGACAG | TAAATCTGTG | TGGGGCTAGA | ACAAAAATTA | AGACATGTTT | GGCAATATTT | 1380 |
| CAGTTAGTTA | AATACCTGTA | GCCTAACTGG | AAAATTCAGG | CTTCATCATG | TAGTTTG | 1437 |

(2) INFORMATION FOR SEQ ID NO:5:

(i) SEQUENCE CHARACTERISTICS:
(A) LENGTH: 359 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:5:

Met Ser Met Asn Asn Ser Lys Gln Leu Val Ser Pro Ala Ala Ala Leu
1               5                   10                  15

Leu Ser Asn Thr Thr Cys Gln Thr Glu Asn Arg Leu Ser Val Phe Phe
            20                  25                  30

Ser Val Ile Phe Met Thr Val Gly Ile Leu Ser Asn Ser Leu Ala Ile
        35                  40                  45

Ala Ile Leu Met Lys Ala Tyr Gln Arg Phe Arg Gln Lys Ser Lys Ala

|     |     |     |     |     | 50  |     |     |     |     | 55  |     |     |     |     | 60  |
| --- | --- | --- | --- | --- | --- | --- | --- | --- | --- | --- | --- | --- | --- | --- | --- |
| Ser 65 | Phe | Leu | Leu | Leu 70 | Ala | Ser | Gly | Leu | Val | Ile 75 | Thr | Asp | Phe | Phe | Gly 80 |
| His | Leu | Ile | Asn | Gly 85 | Ala | Ile | Ala | Val | Phe 90 | Val | Tyr | Ala | Ser | Asp 95 | Lys |
| Glu | Trp | Ile | Arg 100 | Phe | Asp | Gln | Ser | Asn 105 | Val | Leu | Cys | Ser | Ile 110 | Phe | Gly |
| Ile | Cys | Met 115 | Val | Phe | Ser | Gly | Leu 120 | Cys | Pro | Leu | Leu | Leu 125 | Gly | Ser | Val |
| Met | Ala 130 | Ile | Glu | Arg | Cys | Ile 135 | Gly | Val | Thr | Lys | Pro 140 | Ile | Phe | His | Ser |
| Thr 145 | Lys | Ile | Thr | Ser | Lys 150 | His | Val | Lys | Met | Met 155 | Leu | Ser | Gly | Val | Cys 160 |
| Leu | Phe | Ala | Val | Phe 165 | Ile | Ala | Leu | Leu | Pro 170 | Ile | Leu | Gly | His | Arg 175 | Asp |
| Tyr | Lys | Ile | Gln 180 | Ala | Ser | Arg | Thr | Trp 185 | Cys | Phe | Tyr | Asn | Thr 190 | Glu | Asp |
| Ile | Lys | Asp 195 | Trp | Glu | Asp | Arg | Phe 200 | Tyr | Leu | Leu | Leu | Phe 205 | Ser | Phe | Leu |
| Gly | Leu 210 | Leu | Ala | Leu | Gly | Val 215 | Ser | Leu | Leu | Cys | Asn 220 | Ala | Ile | Thr | Gly |
| Ile 225 | Thr | Leu | Leu | Arg | Val 230 | Lys | Phe | Lys | Ser | Gln 235 | Gln | His | Arg | Gln | Gly 240 |
| Arg | Ser | His | His | Leu 245 | Glu | Met | Val | Ile | Gln 250 | Leu | Leu | Ala | Ile | Met 255 | Cys |
| Val | Ser | Cys | Ile 260 | Cys | Trp | Ser | Pro | Phe 265 | Leu | Val | Thr | Met | Ala 270 | Asn | Ile |
| Gly | Ile | Asn 275 | Gly | Asn | His | Ser | Leu 280 | Glu | Thr | Cys | Glu | Thr 285 | Thr | Leu | Phe |
| Ala | Leu 290 | Arg | Met | Ala | Thr | Trp 295 | Asn | Gln | Ile | Leu | Asp 300 | Pro | Trp | Val | Tyr |
| Ile 305 | Leu | Leu | Arg | Lys | Ala 310 | Val | Leu | Lys | Asn | Leu 315 | Tyr | Lys | Leu | Ala | Ser 320 |
| Gln | Cys | Cys | Gly | Val 325 | His | Val | Ile | Ser | Leu 330 | His | Ile | Trp | Glu | Leu 335 | Ser |
| Ser | Ile | Lys | Asn 340 | Ser | Leu | Lys | Val | Ala 345 | Ala | Ile | Ser | Glu | Ser 350 | Pro | Val |
| Ala | Glu | Lys 355 | Ser | Ala | Ser | Thr |     |     |     |     |     |     |     |     |     |